United States Patent [19]

Schepel et al.

[11] Patent Number: 5,135,540
[45] Date of Patent: Aug. 4, 1992

[54] INTRAOCULAR LENS

[75] Inventors: Siebe J. Schepel, Leek; Lieuwe P. Jonkman, Roden, both of Netherlands

[73] Assignee: Kabi Pharmacia AB, Uppsala, Sweden

[21] Appl. No.: 784,881

[22] Filed: Oct. 30, 1991

Related U.S. Application Data

[63] Continuation of Ser. No. 490,577, filed as PCT/NL90/00005, Jan. 12, 1990

[30] Foreign Application Priority Data

Jan. 13, 1989 [NL] Netherlands ............... 8900082

[51] Int. Cl.⁵ ............................................. A61F 2/16
[52] U.S. Cl. .................................................. 623/6
[58] Field of Search ................................... 623/6

[56] References Cited

U.S. PATENT DOCUMENTS 4,435,855  3/1984  Pannu ............................ 623/6

FOREIGN PATENT DOCUMENTS 0061282  9/1982  European Pat. Off. ......... 623/6
0246216  11/1987  European Pat. Off. ......... 623/6
0289449  11/1988  European Pat. Off. ......... 623/6
8500527  1/1986  Netherlands ..................... 623/6

Primary Examiner—Randy C. Shay
Attorney, Agent, or Firm—Fred Philpitt

[57] ABSTRACT

An intraocular lens having a substantially circular optical portion and two separate fixation arms each having an inner end and an outer free end. The fixation arms are each attached to the optical portion via a short connecting member which extends substantially radially from the optical portion circumference and is of approximately the same thickness and flexibility as the fixation arm to which it is attached.

1 Claim, 1 Drawing Sheet

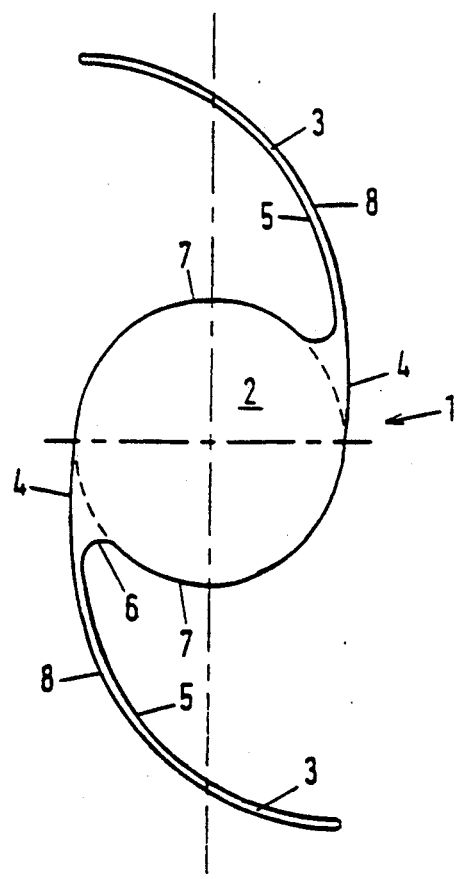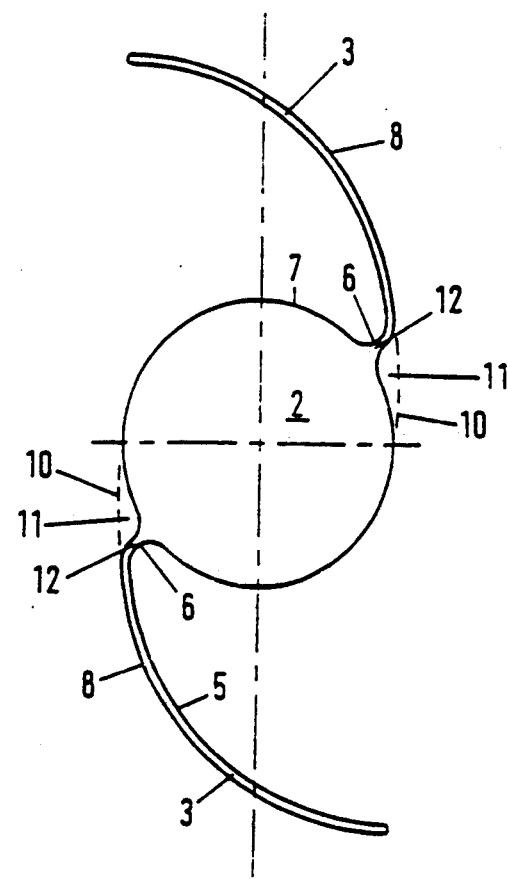
FIG.1 PRIOR ART
FIG.2

INTRAOCULAR LENS

This is a continuation of application Ser. No. 07/490,577, filed as PCT/NL90/00005, Jan. 12, 1990 and the benefits of 35 USC 120 are claimed relative to it.

This invention relates to an implantable intraocular lens comprising an optical portion having a substantially circular circumference and a plurality of fixation element connected to said optical portion along the circumference thereof.

In a cataractic eye, the lens is opacified and is removed. The absence of the lens is then compensated for by introducing an artificial lens, the so-called intraocular lens. The intraocular lens is implanted by means of surgery, often together with the removal of the opacified natural lens. The intraocular lenses can be implanted in the anterior chamber, in the pupil, or in the posterior chamber. In the last case, which is preferred in the great majority of cases at present, the intraocular lens can be placed either within the so-called capsular bag or between the capsular bag and the iris. The capsular bag is a membrane surrounding the lens proper, which is often left in the eye, at least in the case of extracapsular extraction, when the opacified lens is removed.

An artificial intraocular lens consists of a central optical portion and fixation members or haptic members. These members may be made separately and then interconnected, or may be made of the same piece of material.

In the first case, the lens is sometimes referred to as a three-piece lens, at least if, two fixation members are used. In the second case the lens would be called a one-piece lens.

The haptic elements provide for the suspension of the lens at a suitable position within the eye. The shape of these elements, often referred to as loops, is partly determined by the position within the eye where the lens is implanted. The way in which the intraocular lens is made also affects the shape of the loops. A three-piece lens comprises an optical portion, mostly made of polymethylmethacrylate (PMMA) and loops, mostly of prolene, threaded through and fixed in holes in the optical portion. A one-piece lens often consists of PMMA only. In this case the loops are formed by starting from round blanks and removing so much material as to leave the optical portion and the loops. The transition of a loop to the optical portion is therefore of a different nature from a multi-piece lens. As a result, the rigidity of the loop close to the transition to the optical portion has a different character from the other types of lenses referred to.

More particularly, in prior implantable intraocular lenses of the one-piece type, the place where a loop is attached to the optical portion, or the lens body, is rigidified and broadened relatively to the loop, so that the loop is relatively stiff adjacent to the point of attachment.

U.S. Pat. No. 4,435,855 and U.S. Pat. No. 4,370,760 describe implantable intraocular lenses of the one-piece type in which the loops connect approximately tangentially to the lens body and for the rest extend in a so-called C bend or J bend relatively to the lens body. Adjacent to the point of attachment, the loops are broadened fan-wise so to say.

As a result of this design, the mobility of the loops relative to the lens body is limited close to the lens body, which may be a drawback during the implantation of such lenses, especially when it is desired to make a small incision in the cornea.

Furthermore, as a result of this design, the lens can be properly gripped by means of conventional tools during implantation on the inside of the loop, but not on its outside.

SUMMARY OF THE INVENTION

It is an object of the present invention to overcome the disadvantage outlined above and, in general, to provide an effective one-piece intraocular lens which is simple and efficient to implant, and requires a relatively small incision in the eye.

To this effect, according to the invention, an intraocular lens of the type described is characterized in that, at the point of the connection between at least one curved arm and the optical portion, material has been removed in an area located in alignment with the arm, but outside the circular circumference of the optical portion, so that the arm is connected to the optical portion through a relatively thin and short connecting member.

As a result of the greater flexibility of the loop at the transition to the optical portion, which is thus obtained, it is possible for the loop to be flexed further over the optical portion, in a similar manner to a multi-piece lens.

The intraocular lens can thus be made smaller during its introduction. As furthermore, as will be explained hereinafter, the diameter of the optical portion can be made relatively small, a lens is obtained which can be introduced into the capsular bag in a simpler manner, and for which during the operation a relatively small incision needs to be made in the cornea. Small incisions are important because they mitigate post-operative problems for the patient. Small incisions are used in operations in which the opacified lens is removed through pulverisation (phaco-emulsification). If a phaco-operation is followed by the implantation of a large intraocular lens, the advantage of the phaco-operation technique is at least partly lost. The invention enhances the usefulness of operations with smaller incisions and by the phaco technique.

The advantage over and above the multi-piece lens, which already has the greater flexibility referred to, is that the diameter of the optical portion may be smaller without reducing the effective part of the optical portion. In fact, in the case of multi-piece lenses, some part of the lens is always used for securing the loops, mostly blind holes, drilled in the optical portion, which reduces its effective diameter.

BRIEF DESCRIPTION OF THE DRAWINGS

The invention will be described in more detail hereinafter with reference to the accompanying drawings. In said drawings, FIG. 1 diagrammatically shows a one-piece implantable intraocular lens of the prior art; and FIG. 2 diagrammatically shows a first embodiment, by way of example, of an implantable intraocular lens according to the present invention.

DESCRIPTION OF THE PREFERRED EMBODIMENTS

FIG. 1 shows diagrammatically a known one-piece intraocular lens 1 which can be implanted in an eye to replace a clouded natural lens. The known lens comprises an optical portion or lens body 2 provided with a plurality, in this example two, fixation elements 3. The fixation elements 3 have the shape of thin, curved and flexible arms connected approximately tangentially to the substantially circular circumference of the lens body. The fixation elements and the lens body are made in one piece. For this purpose, the starting product may, for example, be a disk-shaped blank. At the junctions 4, where the arms 3 connect with the lens body 2, the arms 3 have a broadened shape, because, on the side 5 facing the lens body the arms connect through a returning curvature 6 with the circumference 7 of the lens body, whereas on the side 8 away from the lens body, the arms connect smoothly, approximately tangentially, with the circumference of the lens body. In this way a junction 4 occupies a considerable part of the circumference of the lens body 2. In the example shown, each junction 4 occupies approximately one-eighth of the circumference of the lens body.

It is true that the design described ensures a firm connection between the arms 3 and the lens body 2, but at the same time the mobility of the arms relative to the lens body is limited.

FIG. 2 shows an embodiment of an intraocular eye lens according to the present invention. In FIG. 2, corresponding parts are designed by the same reference numerals as in FIG. 1. The embodiment shown in FIG. 2 differs from the known intraocular lens shown in FIG. 1 in that, at the junction of the arms, material 11 has been removed on the outside. For purposes of clarification, the situation corresponding to FIG. 1 is shown in dotted lines 10.

As a result of the removal of the material 11, the arms 3 no longer connect to the lens body with a broadened end, but they are, as it were, connected to the lens body through a relative thin and short connecting member 12. In this example, the connecting members 12 extend approximately transversely to the circumference 7 of lens body 2 and, in this example, have approximately the same thickness as the rest of the arms. As a consequence, the connecting members may have substantially the same flexibility as the arms proper and permit a relatively great movability of the arms relatively to the lens body. The arms of an intraocular lens according to this invention, for example, can be flexed over the lens body to a very great extent, which facilities their being implanted through a relatively small incision.

If desired, starting from the shape shown in FIG. 1, further material may be removed on the inside of the arms, at 6.

An additional advantage of the lenses according to the present invention is that they can be gripped by the arms very closely to the optical portion by means of tools used during implantation, such as Sinskey hook.

In addition, owing to the orientation of the fixation members relative to the optical portion, the lens can be so gripped by means of a hook that the lens can be rotated in two direction.

It is noted that, after reading the foregoing, various modifications will readily occur to those skilled in the art. Thus, for example, the ends of the arms may be provided with round disks or eyelets, or connect to an additional arm portion, as described in U.S. Pat. No. 4,435,855 or U.S. Pat. No. 4,370,760.

We claim:
1. An implantable one-piece intraocular lens comprising
  (a) a central optical portion (7) having a substantially circular circumference,
  (b) two separate fixation members (3) in the form of elongated arms positioned outwardly from the circumference of said optical portion (7), each fixation member (3) having an inner end and an outer free end, and each fixation member (3) being disposed in a smooth arcuate curve that starts at a point close to the central optical portion (7) and thereafter is continuously spaced a greater and greater distance away from said central optical portion (7) until the outer free end of the fixation member (3) is reached,
  (c) a connecting member (12) connecting the inner end of each fixation member (3) to the optical potion (7),
    (1) each connecting member (12) extending substantially radially outwardly from the circumference of said optical portion (7) and being joined to the inner end of a fixation member (3) at an angle so that the connecting member (12) is disposed along a line which would not merely be an extension of said smooth arcuate curve of the fixation member (3) to which it is connected,
    (2) the length of each connecting member (12) being short in comparison to the length of the fixation member (3) to which it is attached, and
    (3) each connecting member (12) having approximately the same thickness and flexibility as the fixation member (3) to which it is attached.

* * * * *